US008323627B2

(12) United States Patent
Dumont et al.

(10) Patent No.: US 8,323,627 B2
(45) Date of Patent: Dec. 4, 2012

(54) MONOESTER OF N-UNDECYLENOYL PHENYLALANINE AND POLYOL, METHOD FOR PREPARING SAME, AND USE OF SAID ESTERS AS A SKIN LIGHTENING AGENT

(75) Inventors: Sandy Dumont, Caucalieres (FR); Cecile Taillebois, Castres (FR); Jerome Guilbot, Castres (FR); Corinne Stoltz, Thiais (FR); Sebastien Kerverdo, Vincennes (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 141 days.

(21) Appl. No.: 13/063,800

(22) PCT Filed: Sep. 14, 2009

(86) PCT No.: PCT/FR2009/051717
§ 371 (c)(1),
(2), (4) Date: Mar. 14, 2011

(87) PCT Pub. No.: WO2010/034917
PCT Pub. Date: Apr. 1, 2010

(65) Prior Publication Data
US 2011/0171150 A1    Jul. 14, 2011

(30) Foreign Application Priority Data
Sep. 24, 2008   (FR) ..................... 08 56420

(51) Int. Cl.
A61Q 19/02      (2006.01)
C07C 229/00     (2006.01)
(52) U.S. Cl. .......................... 424/62; 560/40
(58) Field of Classification Search ............ 424/62; 560/39
See application file for complete search history.

(56) References Cited

U.S. PATENT DOCUMENTS

| | | | |
|---|---|---|---|
| 5,266,576 A * | 11/1993 | Vincent et al. ............ 514/300 |
| 5,888,482 A | 3/1999 | Amalric et al. | |
| 5,958,431 A | 9/1999 | Brancq et al. | |
| 6,245,821 B1 | 6/2001 | Bulcourt et al. | |
| 6,268,400 B1 | 7/2001 | Amalric et al. | |
| 6,353,034 B1 | 3/2002 | Amalric et al. | |
| 6,464,993 B1 | 10/2002 | Milius et al. | |
| 6,488,946 B1 | 12/2002 | Milius et al. | |
| 2001/0039337 A1 | 11/2001 | Milius et al. | |
| 2003/0133957 A1 | 7/2003 | Amalric et al. | |
| 2004/0265259 A1 | 12/2004 | Rose et al. | |
| 2005/0069512 A1 | 3/2005 | Roso et al. | |
| 2005/0101727 A1 | 5/2005 | Amalric et al. | |
| 2005/0118119 A1* | 6/2005 | Stoltz et al. ............ 424/62 |
| 2006/0263321 A1* | 11/2006 | Bissett ............ 424/70.13 |
| 2007/0161543 A1* | 7/2007 | Yu et al. ............ 514/7 |
| 2007/0282002 A1* | 12/2007 | Maezono et al. ............ 514/563 |

FOREIGN PATENT DOCUMENTS

| | | |
|---|---|---|
| EP | 0499521 A1 | 8/1992 |
| EP | 1 471 881 B1 | 10/2008 |
| FR | 2 668 080 A1 | 4/1992 |
| FR | 2 734 496 A1 | 11/1996 |
| FR | 2 756 195 A1 | 5/1998 |
| FR | 2 762 317 A1 | 10/1998 |
| FR | 2 784 680 A1 | 4/2000 |
| FR | 2 784 904 A1 | 4/2000 |
| FR | 2 790 977 A1 | 9/2000 |
| FR | 2 791 565 A1 | 10/2000 |
| FR | 2 804 432 A1 | 8/2001 |
| FR | 2 807 435 A1 | 10/2001 |
| FR | 2 820 316 A1 | 8/2002 |
| FR | 2 830 445 A1 | 4/2003 |
| FR | 2 830 774 A1 | 4/2003 |
| FR | 2 852 257 A1 | 9/2004 |
| FR | 2 852 258 A1 | 9/2004 |
| FR | 2 858 554 A1 | 2/2005 |
| JP | 2000/229121 A | 8/2000 |
| WO | 03/061768 A | 7/2003 |

OTHER PUBLICATIONS

Preliminary Report on Patentability (English) (WIPO, Dec. 6, 2011), 7 pages.*
International Search Report (English) (WIPO, Oct. 4, 2011), 2 pages.*
Espacenet-INPADOC patent family for FR 2839447 A1 [Downloaded Sep. 19, 2012], 1 page.*
Espacenet-INPADOC patent family for FR 2900413 A1 [Downloaded Sep. 19, 2012], 2 pages.*
Jerome Guilbot, Imporetance des corps grans dans le domaine des tensioactifs, OCL (Oleagineux Corps Gras Lipides) vol. 13, No. 2-3, (Mar.-Jun. 2006), pp. 178-186; cited because it teaches lipo amino acids (see pp. 184-185), 10 pages.*
International Search Report, dated Oct. 4, 2011, in PCT/FR2009/051717.

* cited by examiner

*Primary Examiner* — Jason M Sims
*Assistant Examiner* — Miriam A Levin
(74) *Attorney, Agent, or Firm* — Young & Thompson

(57) ABSTRACT

A compound of the formula (I):

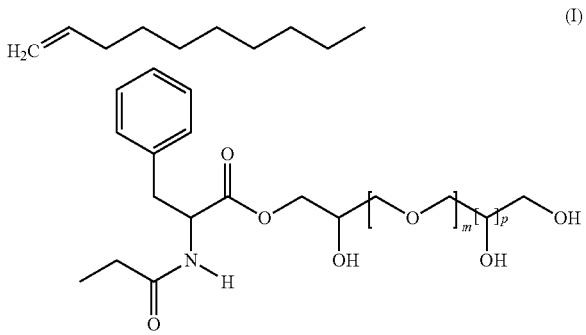

where m is an integer equal to 0 or 1, and p is an integer equal to 0, 1, 2 or 3. A method for preparing the compound of the formula (I), and the use thereof as a skin lightening agent. A cosmetic composition and a drug containing the compound of the formula (I).

16 Claims, No Drawings

MONOESTER OF N-UNDECYLENOYL PHENYLALANINE AND POLYOL, METHOD FOR PREPARING SAME, AND USE OF SAID ESTERS AS A SKIN LIGHTENING AGENT

The present invention relates to a novel cosmetic active agent that is capable of lightening the skin.

The majority of commercial skin-lightening cosmetic formulations are based on kojic acid, arbutin or magnesium ascorbyl phosphate.

The European patent application published under the number EP 1 471 881 discloses that N-acyl derivatives of α-amino acids and especially N-undecylenoyl phenylalanine show affinity toward the Melanocyte Specific Hormone (α-MSH) receptor and thus induce lightening of the skin according to the following biochemical mechanism: competition between the hormone α-MSH and the molecule with affinity toward the α-MSH receptor leads to a reduced degree of binding of said hormone to the cell receptors; this composition has the consequence of inhibiting the activity of adenylate cyclase, which leads to reduced conversion of ATP into intracellular cyclic AMP; the decrease in the level of cyclic AMP leads to inhibition of the enzyme Protein Kinase A (PKA); the inhibition of Protein Kinase A induces reduced activation of tyrosinase due to the reduced conversion of the latter into phosphorylated tyrosinase; this reduced activation of tyrosinase leads to a decrease in melanin synthesis, resulting in reduced pigmentation of the skin.

Japanese patent application No. 2000-229121 describes the use of polyol esters of N-acylamino acids as efficient surfactants (paragraph [00003] of said application).

In the context of their studies on novel skin-lightening active agents, which are improved relative to those mentioned above, without deteriorating their cutaneous tolerance, the inventors have developed the compounds that are the subject of the present invention.

Accordingly, according to a first aspect, one subject of the invention is a compound of formula (I):

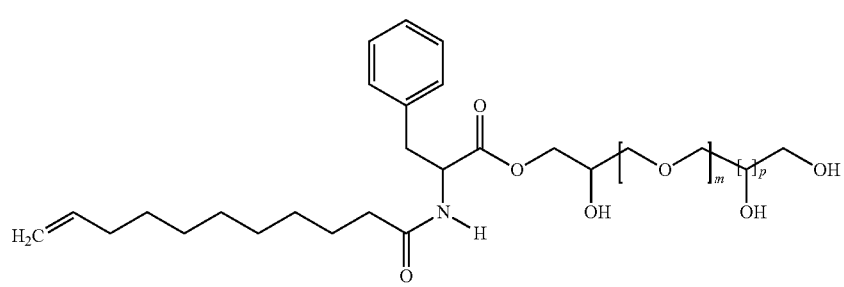

(I)

in which m is an integer equal to 0 or 1 and p is an integer equal to 0, 1, 2 or 3.

According to one particular aspect of the present invention, a subject thereof is a compound of formula ($I_a$):

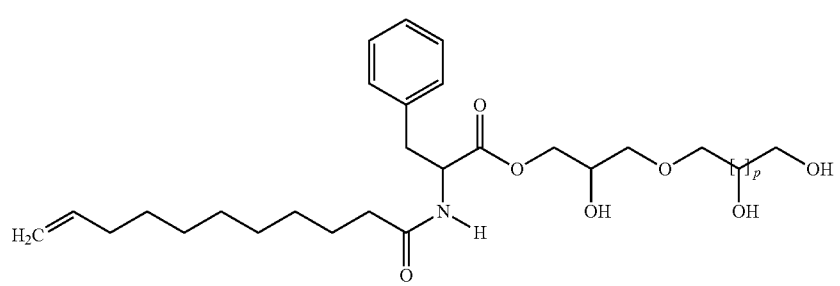

($I_a$)

corresponding to formula (I) as defined previously, in which m is equal to 1.

According to another particular aspect of the present invention, a subject thereof is a compound of formula ($I_b$):

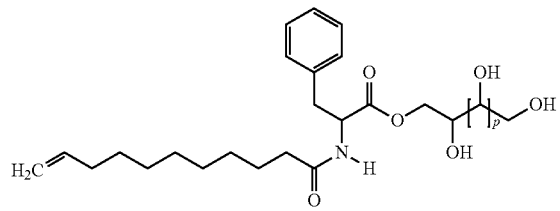

($I_b$)

corresponding to formula (I) as defined previously, in which m is equal to 0.

According to another particular aspect of the present invention, a subject thereof is a compound of formula ($I_{b1}$):

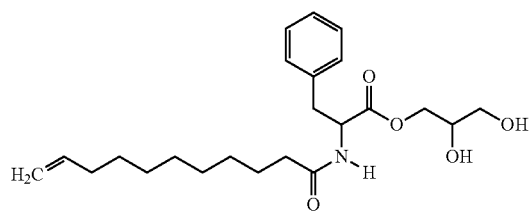

($I_{b1}$)

corresponding to formula ($I_b$) as defined previously, in which p is equal to 0.

According to another particular aspect of the present invention, a subject thereof is a compound of formula ($I_{a1}$):

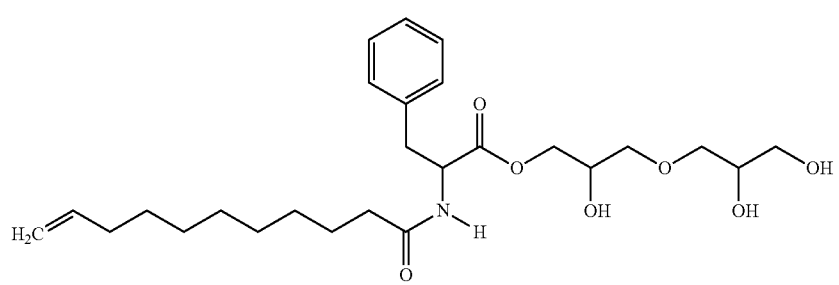

($I_{a1}$)

corresponding to formula ($I_a$) as defined previously, in which p is equal to 1.

According to another particular aspect of the present invention, a subject thereof is a compound of formula ($I_{b2}$):

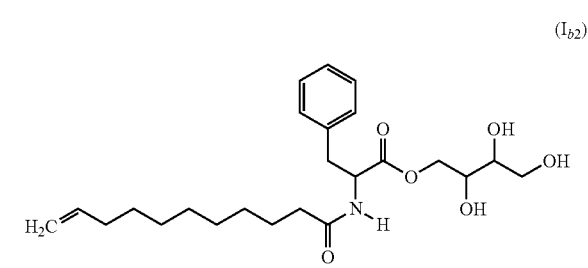

($I_{b2}$)

corresponding to formula ($I_b$) as defined previously, in which p is equal to 1.

According to another particular aspect of the present invention, a subject thereof is a compound of formula ($I_{b3}$):

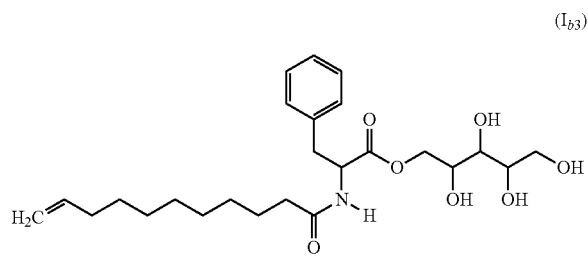

($I_{b3}$)

corresponding to formula ($I_b$) as defined previously, in which p is equal to 2.

According to another particular aspect of the present invention, a subject thereof is a compound of formula ($I_{b4}$):

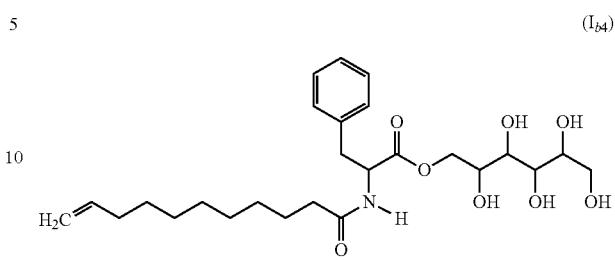

($I_{b4}$)

corresponding to formula ($I_b$) as defined previously, in which p is equal to 3.

A subject of the invention is also a process for preparing the compound of formula (I) as defined previously, comprising:

a step a) of esterification of the compound of formula (II):

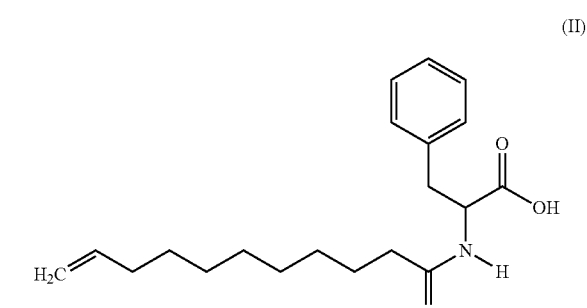

(II)

with the polyol of formula (III):

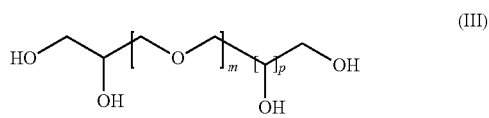

(III)

to form the compound of formula (I) and optionally a compound of formula (IV):

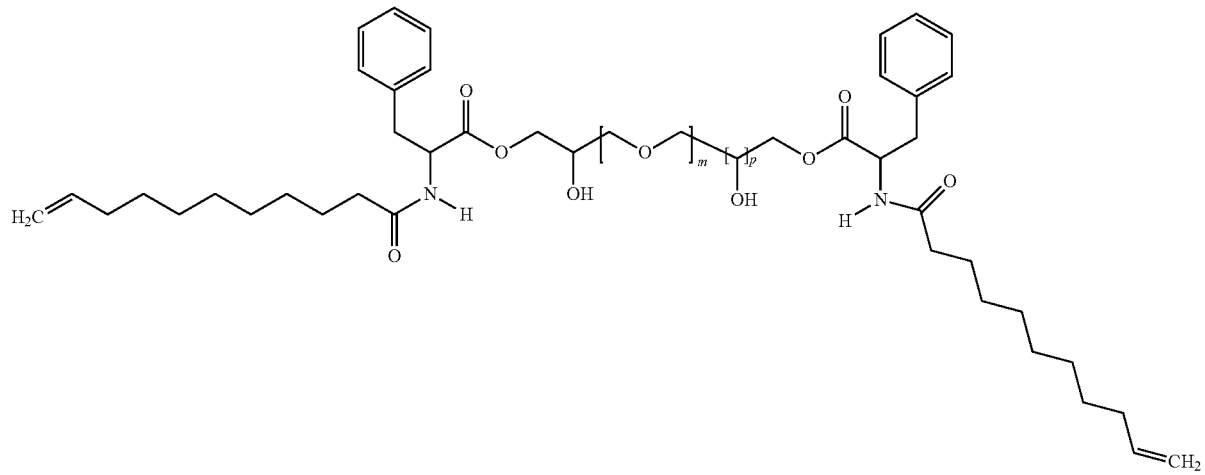

(IV)

and, if desired, a step b) of separation of said compound of formula (IV) and of said compound of formula (I).

In the process as defined above, step a) is generally performed at a temperature of about 100° C. under inert gas and acidic catalysis.

During this step a), it is possible for there also to be formation, but to a lesser extent than for the compound of formula (I), of the compound of formula (IV). The mole ratio of compound of formula (I) to compound of formula (IV) obtained during step a) of the process is generally greater than or equal to 80/20 and often greater than or equal to 90/10.

Step b) of separation of the compounds of formula (I) and of formula (IV) is performed via the standard separation methods known to those skilled in the art.

According to another aspect, a subject of the invention is a cosmetic composition, characterized in that it comprises, as lightening agent for human bodily skin, an effective amount of a compound of formula (I) as defined previously.

According to another aspect, a subject of the invention is a medicament with lightening activity on human bodily skin, comprising as active principle an effective amount of a compound of formula (I) as defined previously.

In the composition and/or the medicament as defined above, the compound of formula (I) is generally used in an amount of between 0.05% by mass and 10% by mass per 100% by mass of the composition, more particularly between 0.5% by mass and 5% by mass per 100% by mass of the composition and most particularly between 1% by mass and 5% by mass per 100% by mass of the composition.

The compositions and/or medicaments as defined above are generally in the form of dilute aqueous or aqueous-alcoholic solutions, in the form of simple or multiple emulsions, such as water-in-oil (W/O), oil-in-water (O/W), oil-in-water-in-oil (O/W/O) or water-in-oil-in-water (W/O/W) emulsions, in which the oil is of plant and/or animal and/or mineral nature, or in the form of powder. They may also be dispersed or impregnated onto fabric or nonwoven materials, whether they are wipes, paper towels or clothing.

The compositions and/or medicaments as defined above are administered to the individual in the conventional forms used in cosmetics and pharmacy; these are more particularly topical administrations.

In general, a compound of formula (I) as defined previously, alone or as a mixture with a compound of formula (IV) as defined previously, is combined with numerous types of adjuvants or active principles used in cosmetic formulations, whether they are fatty substances, organic solvents, thickeners, gelling agents, softeners, antioxidants, opacifiers, stabilizers, foaming and/or detergent surfactants, emollients, fragrances, ionic or nonionic emulsifiers, fillers, sequestrants, chelating agents, preserving agents, essential oils, dyestuffs, pigments, hydrophilic or lipophilic active agents, humectants, for instance glycerol, preserving agents, dyes, cosmetic active agents, mineral and/or organic sunscreens, mineral fillers, for instance iron oxides, titanium oxides and talc, synthetic fillers, for instance Nylons and crosslinked or non-crosslinked poly(methyl methacrylates), silicone elastomers, sericites or plant extracts, or alternatively lipid vesicles, or any other ingredient usually used in cosmetics.

As examples of oils that may be combined with a compound of formula (I) as defined previously, alone or as a mixture with a compound of formula (IV) as defined previously, mention may be made of mineral oils such as liquid paraffin, liquid petroleum jelly, isoparaffins or white mineral oils; oils of animal origin, such as squalene or squalane; plant oils, such as sweet almond oil, coconut oil, castor oil, jojoba oil, olive oil, rapeseed oil, groundnut oil, sunflower oil, wheatgerm oil, corn germ oil, soybean oil, cotton oil, alfalfa oil, poppy oil, pumpkin oil, evening primrose oil, millet oil, barley oil, rye oil, safflower oil, candlenut oil, passionflower oil, hazelnut oil, palm oil, Shea butter, apricot kernel oil, beauty-leaf oil, sysymbrium oil, avocado oil, calendula oil, ethoxylated plant oils; synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, fatty acid monoglycerides, diglycerides and triglycerides, such as glyceryl triheptanoate, alkyl benzoates, poly-α-olefins, polyolefins such as polyisobutene, synthetic isoalkanes such as isohexadecane, identified in Chemical Abstracts by the number RN=93685-80-4 and which is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9), isododecane, hydrogenated polydecene or hydrogenated polyisobutene, sold in France by the company Ets B. Rossow et Cie under the name Parleam-Polysynlane™, mentioned in Michel and Irene Ash; Thesaurus of Chemical Products, Chemical Publishing Co, Inc. 1986 Volume I, page 211 (ISBN 0 7131 3603 0), perfluoro oils; and silicone oils such as dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups.

As another fatty substance that may be combined with a compound of formula (I) as defined previously, alone or as a mixture with a compound of formula (IV) as defined previously, mention may be made of saturated or unsaturated, linear or branched fatty alcohols, and saturated or unsaturated, linear or branched fatty acids.

Among the thickening and/or emulsifying polymers used in the present invention, there are, for example, polymers of polyelectrolyte type, for instance homopolymers or copolymers of acrylic acid or of acrylic acid derivatives, homopolymers or copolymers of methacrylic acid or of methacrylic acid derivatives, homopolymers or copolymers of acrylamide, homopolymers or copolymers of acrylamide derivatives, homopolymers or copolymers of 2-methyl[(1-oxo-2-propenyl)amino]-1-propanesulfonic acid (AMPS), homopolymers or copolymers of vinyl monomers, homopolymers or copolymers of trimethylaminoethyl acrylate chloride; hydrocolloids of plant or biosynthetic origin, for example xanthan gum, karaya gum, carrageenates, alginates, galactomannans; silicates; cellulose and derivatives thereof; starch and hydrophilic derivatives thereof; polyurethanes.

Among the polymers of polyelectrolyte type that may be used in the production of a gelled aqueous phase that can be used in the preparation of W/O, O/W, W/O/W or O/W/O emulsions, or of an aqueous gel containing the compound of formula (I) as defined previously, alone or as a mixture with a compound of formula (IV) as defined previously, there are, for example, copolymers of acrylic acid and of 2-methyl[(1-oxo-2-propenyl)amino]-1-propanesulfonic acid (AMPS), copolymers of acrylamide and of 2-methyl[(1-oxo-2-propenyl)amino]-1-propane-sulfonic acid, copolymers of 2-methyl[(1-oxo-2-propenyl)amino]-1-propanesulfonic acid and of (2-hydroxy-ethyl) acrylate, 2-methyl[(1-oxo-2-propenyl) amino]-1-propanesulfonic acid homopolymer, acrylic acid homopolymer, copolymers of acrylic acid and of N-[2-hydroxy-1,1-bis(hydroxymethyl)ethyl]propenamide [or tris(hydroxymethyl)acrylamidomethane or N-tris(hydroxy-methyl)methylacrylamide, also known as THAM], copolymers of AMPS and of THAM, copolymers of acryloylethyltrimethylammonium chloride and of acrylamide, copolymers of AMPS and of vinylpyrrolidone, copolymers of acrylic acid and of alkyl acrylates whose carbon chain comprises between ten and thirty carbon atoms, copolymers of AMPS and of alkyl acrylates whose carbon chain comprises between ten and thirty carbon atoms. Such polymers are sold, respectively, under the names Simulgel™ EG, Sepigel™ 305, Simulgel™ NS, Simulgel™ 800, Simulgel™ A, Simulgel™ EPG, Simulgel™ INS 100, Simulgel™ FL, Simulgel SMS 88, Sepisoft™ SP, Sepigel™ 501, Sepigel™ 502, Sepiplus™ 250, Sepiplus™ 265, Sepiplus™ 400, Sepinov™ EMT 10, Carbopol™, Ultrez™ 10, Aculyn™, Pemulen™ TR1, Pemulen™ TR2, Luvigel™ EM, Salcare™ SC91, Salcare™ SC92, Salcare™ SC95, Salcare™ SC96, Flocare™ ET100, Flocare™ ET58, Hispagel™, Novemer™ EC1, Aristoflex™ AVC, Aristoflex™ HBM, Rapithix™ A60, Rapithix™ A100, Cosmedia SP, Stabileze™ 06 and Stabileze™ QM.

Among the waxes that may be used in the present invention, mention may be made, for example, of beeswax; carnauba wax; candelilla wax; ouricury wax; Japan wax; cork fiber wax; sugarcane wax; paraffin waxes; lignite waxes; microcrystalline waxes; lanolin wax; ozokerite; polyethylene wax, hydrogenated oils; silicone waxes; plant waxes; fatty alcohols and fatty acids that are solid at room temperature; glycerides that are solid at room temperature.

Among the emulsifiers that may be used in the present invention, mention may be made of optionally alkoxylated alkylpolyglycoside fatty esters, and most particularly ethoxylated methylpolyglucoside esters such as PEG 120 methyl glucose trioleate and PEG 120 methyl glucose dioleate, sold, respectively, under the names Glucamate™ LT and Glucamate™ DOE120alkoxylated fatty esters, such as PEG 150 pentaerythrityl tetrastearate sold under the name Crothix™ DS53, PEG 55 propylene glycol oleate sold under the name Antil™ 141; fatty-chain polyalkylene glycol carbamates such as PPG 14 laureth isophoryl dicarbamate sold under the name Elfacos™ T211, PPG 14 palmeth 60 hexyl dicarbamate sold under the name Elfacos™ GT2125fatty acids, ethoxylated fatty acids, fatty acid esters of sorbitol, ethoxylated fatty acid esters, polysorbates, polyglyceryl esters, ethoxylated fatty alcohols, sucrose esters, alkylpolyglycosides, sulfated and phosphated fatty alcohols or mixtures of alkylpolyglycosides and of fatty alcohols described in French patent applications 2 668 080, 2 734 496, 2 756 195, 2 762 317, 2 784 680, 2 784 904, 2 791 565, 2 790 977, 2 807 435, 2 804 432, 2 830 774 and 2 830 445, combinations of emulsifying surfactants chosen from alkylpolyglycosides, combinations of alkylpolyglycosides and of fatty alcohols, polyglycerol or polyglycol or polyol esters such as the polyglycol or polyglycerol polyhydroxystearates used in French patent applications 2 852 257, 2 858 554, 2 820 316 and 2 852 258.

Among the foaming and/or detergent surfactants that may be used in the present invention, mention may be made of the topically acceptable anionic, cationic, amphoteric or nonionic surfactants usually used in this field of activity.

Among the anionic surfactants that may be used in the present invention, mention will be made particularly of alkali metal salts, alkaline-earth metal salts, ammonium salts, amine salts or amino alcohol salts of the following compounds: alkyl ether sulfates, alkyl sulfates, alkylamido ether sulfates, alkylaryl polyether sulfates, monoglyceride sulfates, α-olefin sulfonates, paraffin sulfonates, alkyl phosphates, alkyl ether phosphates, alkylsulfonates, alkylamidesulfonates, alkylarylsulfonates, alkylcarboxylates, alkylsulfosuccinates, alkyl ether sulfosuccinates, alkylamide-sulfosuccinates, alkylsulfoacetates, alkylsarcosinates, acylisethionates, N-acyltaurates and acyllactylates. Among the anionic surfactants, mention will also be made of lipoamino acids, lipoproteins, lipopeptides, lipoprotein derivatives, protein derivatives, fatty acid salts and acid salts of optionally hydrogenated coconut oil.

Among the amphoteric surfactants that may be used in the present invention, mention will be made particularly of alkylbetaines, alkylamidobetaines, sultaines, alkylamidoalkylsulfobetaines, imidazoline derivatives, phosphobetaines, amphopolyacetates and amphopropionates.

Among the cationic surfactants that may be used in the present invention, mention will be made particularly of quaternary ammonium derivatives.

Among the nonionic surfactants that may be used in the present invention, mention will be made particularly of alkylpolyglycosides, castor oil derivatives, polysorbates, coconut amides, N-alkylamines and amine oxides.

As examples of active principles that may be combined with the compound of formula (I) as defined previously, alone or as a mixture with a compound of formula (IV) as defined previously, mention may be made of other compounds with lightening or depigmenting activity, for instance arbutin, kojic acid, hydroquinone, ellagic acid, vitamin C and derivatives thereof, magnesium ascorbyl phosphate, Sepiwhite™ MSH, Sepicalm™ VG, polyphenol extracts, grape extracts, pine extracts, wine extracts, olive extracts, grape-cake extracts, apple juice extracts, N-acyl proteins, N-acyl peptides, N-acylamino acids, for instance N-lauroyl proline, N-linoleyl lysine, N-linoleyl leucine, N-octanoyl glycine, N-undecylenoyl phenylalanine or N-palmitoyl proline, partial hydrolyzates of N-acyl proteins, amino acids, peptides, total protein hydrolyzates, partial protein hydrolyzates, polyols (for instance glycerol or butylene glycol), urea, pyrrolidonecarboxylic acid or derivatives of this acid, glycyrrhetinic acid, α-bisabolol, sugars or sugar derivatives, poly-saccharides or derivatives thereof, hydroxy acids, for instance lactic acid, vitamins, vitamin derivatives, for instance retinol, retinol derivatives, vitamin E and derivatives thereof, minerals, enzymes, coenzymes, for instance coenzyme Q10 and derivatives thereof, hormones or "hormone-like" substances, soybean extracts, for instance Raffermine™, wheat extracts, for instance Tensine™ or Gliadine™, plant extracts, such as tannin-rich extracts, isoflavone-rich extracts or terpene-rich extracts, extracts of freshwater or seawater algae, essential waxes, bacterial extracts, minerals, lipids in general, lipids such as ceramides or phospholipids, active agents with slimming activity, for instance caffeine or its derivatives, active agents with antimicrobial activity or with purifying action on greasy skin, such as Deepaline™ PVB, Lipacide™ UG, active agents with an energizing or stimulatory property, for instance Sepitonic™ M3 or Physiogenyl™, panthenol and its derivatives, for instance Sepicap™ MP, antiaging active agents, for instance Sepilift™ DPHP, Deepaline™ PVB, Sepivinol™ or Sepivital™, moisturizing active agents, for instance Sepicalm™ S, Sepicalm™ VG and Sepilift™ DPHP, Aquaxyl™, Proteol™ SAV 50, anti-ageing active agents, active agents with immediate tightening or smoothing action on the skin, such as Sesaflash™, "anti-photoageing" active agents, active agents for protecting the integrity of the dermo-epidermal junction, active agents for increasing the synthesis of components of the extra-cellular matrix, active agents with slimming, firming or draining activity, such as caffeine, theophylline, cyclic adenosine monophosphate (cAMP), green tea, sage, ginkgo biloba, ivy, common horse chestnut, bamboo, ruscus, butcher's broom, Centella asiatica, heather, meadowsweet, rockweed, rosemary, willow, extracts of parsnip, active agents that create a "heating" sensation on the skin, such as cutaneous capillary circulation activators (for instance nicotinates) or products that create a "freshness" sensation on the skin (for instance menthol and derivatives thereof), active agents with action on stem cells, active agents with action on the epidermis, the dermis, the hypodermis and the cutaneous appendages (bodily hair, sebaceous glands, pores, etc.), and active agents with action on the cutaneous flora.

As sunscreens that may be incorporated into the composition according to the invention, mention may be made of any of those featured in the Cosmetic Directive 76/768/EEC amended appendix VII.

A subject of the invention is also the use of a compound of formula (I) as defined previously as an active agent for lightening human bodily skin.

Finally, a subject of the invention is a non-therapeutic process for lightening human skin, comprising at least one step of applying to said human skin a cosmetic composition for topical use comprising an effective amount of a compound of formula (I) as defined previously.

In the process as described above, the composition is spread onto the surface of the skin to be treated, and the skin is then massaged for a few moments.

As shown by the following examples, the compounds used in the cosmetic or therapeutic treatments defined previously are characterized, unexpectedly, by skin-lightening activity whose intensity may be modified, in contrast with that of the compositions of the prior art, comprising the compound not esterified with a polyol. They are thus generally suitable for treatments intended for lightening the skin, especially by depigmentation and more particularly for fading out or attenuating colored marks appearing on elderly skin.

The experimental study that follows illustrates the invention without, however, limiting it.

EXAMPLE 1

Preparation of N-undecylenoyl phenylalanine monoglyceride [Compound A of Formula $(I_{b1})$]

780 g of N-undecylenoyl phenylalanine, i.e. one molar equivalent, are placed in a jacketed glass reactor, in which flows a heat-exchange fluid, equipped with an efficient stirrer and a device for bubbling nitrogen into the bottom of the reactor, at a temperature of 125° C. to enable total melting of the N-undecylenoyl phenylalanine. 218 g of glycerol, i.e. one molar equivalent, are then introduced onto the N-undecylenoyl phenylalanine at a temperature of about 120° C. The mixture thus prepared is then stirred at a stirring speed of about 300 rpm, with bubbling of nitrogen into the bottom of the reactor, so as to obtain a homogeneous appearance. The homogeneous mixture is maintained at a temperature of 120° C. for 30 minutes, and 2.2 g of 50% hypophosphorous acid and 2.2 g of 98% sulfuric acid are then introduced into the homogeneous mixture prepared previously. The reaction medium is placed under a partial vacuum of 20 mbar (0.2 Pa) and maintained at a temperature of 120° C. for a duration of 20 hours with evacuation of the water formed by means of distillation apparatus. The reaction medium is then emptied out and the analytical characteristics measured are as follows:

aspect at 20° C.: cloudy liquid acid number (according to NFT 60-204)=15.3 mg KOH/g hydroxyl number (according to US Pharmacopeia XXI NF XVI 01/01/1985)=278.3 mg KOH/g saponification number (according to NFT 60-206)=147.2 mg KOH/g iodine number (according to NFT 60-203)=64 g $I_2$/100 g residual glycerol content (by steric exclusion chromatography)=5.6% degree of conversion of the N-undecylenoyl phenylalanine: ≧90% mass ratio of monoglyceride obtained/diglyceride obtained: ≧85/15 monoglyceride obtained (MW=405)/diglyceride obtained (MW=718) mole ratio: 91/9

EXAMPLE 2

Preparation of N-undecylenoyl phenylalanine diglyceryl ester [Compound B of Formula ($I_{a1}$)]

300.0 g of N-undecylenoyl phenylalanine, i.e. one molar equivalent, are placed in a jacketed glass reactor, in which circulates a heat-exchange fluid, equipped with an efficient stirrer and a device for bubbling nitrogen into the bottom of the reactor, at a temperature of 125° C. to enable total melting of the N-undecylenoyl phenylalanine. 159.4 g of diglycerol, i.e. one molar equivalent, are then introduced onto the N-undecylenoyl phenylalanine at a temperature of about 120° C. The mixture thus prepared is then stirred at a stirring speed of about 300 rpm, with bubbling of nitrogen into the bottom of the reactor, so as to obtain a homogeneous aspect. The homogeneous mixture is maintained at a temperature of 120° C. for 30 minutes, and 1.64 g of 50% hypophosphorous acid and 1.49 g of 98% sulfuric acid are then introduced into the homogeneous mixture prepared previously. The reaction medium is placed under a partial vacuum of 20 mbar (0.2 Pa) and maintained at a temperature of 120° C. for a duration of 20 hours, with evacuation of the water formed by means of distillation apparatus.

The reaction medium is then emptied out and the analytical characteristics measured are as follows:

aspect at 20° C.: cloudy liquid acid number (according to NFT 60-204)=16.7 mg KOH/g hydroxyl number (according to US Pharmacopeia XXI NF XVI 01/01/1985)=341.8 mg KOH/g saponification number (according to NFT 60-206)=122 mg KOH/g iodine number (according to NFT 60-203)=53 g $I_2$/100 g residual diglycerol content (by gas chromatography) =24.2%

EXAMPLE 3

Preparation of the erythritol monoester of N-undecylenoyl phenylalanine [Compound C of Formula ($I_{b2}$)]

The process is performed in a manner similar to that of example 1, starting with 780 g of N-undecylenoyl phenylalanine and 288 g of erythritol, i.e. one molar equivalent, and the expected ester is obtained, which has the following analytical characteristics:

aspect at 20° C.: paste-solid acid number (according to NFT 60-204)=18.7 mg KOH/g hydroxyl number (according to US Pharmacopeia XXI NF XVI 01/01/1985)=348.7 mg KOH/g saponification number (according to NFT 60-206)=139.2 mg KOH/g iodine number (according to NFT 60-203)=61 g $I_2$/100 g

EXAMPLE 4

Preparation of the xylitol monoester of N-undecylenoyl phenylalanine [Compound D of Formula ($I_{b3}$)]

The process is performed in a manner similar to that of example 1, starting with 780 g of N-undecylenoyl phenylalanine and 358 g of xylitol, i.e. one molar equivalent, and the expected ester is obtained, which has the following analytical characteristics:

aspect at 20° C.: paste-solid acid number (according to NFT 60-204)=20.8 mg KOH/g hydroxyl number (according to US Pharmacopeia XXI NF XVI 01/01/1985)=466.9 mg KOH/g saponification number (according to NFT 60-206)=126.4 mg KOH/g iodine number (according to NFT 60-203)=52 g $I_2$/100 g

EXAMPLE 5

Preparation of N-undecylenoyl phenylalanine monoglyceride with sorbitol [Compound E of Formula ($I_{b4}$)]

The process is performed in a manner similar to that of example 1, starting with 780 g of N-undecylenoyl phenylalanine and 429 g of sorbitol, i.e. one molar equivalent, and the expected ester is obtained, which has the following analytical characteristics:

aspect at 20° C.: paste-solid acid number (according to NFT 60-204)=21.4 mg KOH/g hydroxyl number (according to US Pharmacopeia XXI NF XVI 01/01/1985)=520.3 mg KOH/g saponification number (according to NFT 60-206)=120.9 mg KOH/g iodine number (according to NFT 60-203)=48 g $I_2$/100 g

Study of the Depigmenting Activity of the Compound of Formula (I) in B16/F1 melanocyte Cultures The influence of N-undecylenoyl phenylalanine monoglyceride, arbutin and N-undecylenoyl phenylalanine on the production of extracellular melanin, in B16/F1 melanocyte cultures, was compared.

Mouse melanocytes of the B16/F1 line cultured as monolayers are seeded in 96-well culture plates at a density of 1500 cells/well. The cells are cultured in a culture medium (MCM medium) at 37° C. under a humid atmosphere containing 5% $CO_2$. The cells are used at 50% of confluence. The MCM medium has the following composition: DMEM medium (Dulbecco's Modified Eagle's Medium) containing 4.5 g/l of glucose supplemented with L-glutamine (2 mM), penicillin (50 IU/ml), streptomycin (50 µg/ml) and fetal calf serum (10% v/v). N-Undecylenoyl phenylalanine monoglyceride, arbutin and N-undecylenoyl phenylalanine are tested at 40 µg/ml in MCM medium. The melanocyte cultures are incubated in the presence of the test product or of the reference products for 72 hours at 37° C., under a humid atmosphere containing 5% $CO_2$. Control cultures are incubated, in the absence of product, in the MCM medium. These control cultures are prepared on each culture plate. Each test is performed six times. After incubation for 72 hours, the incubation media of the cells (n=6) are taken up and stored at −80° C. until the time of evaluation of the effects. The extracellular melanin is quantified by spectrophotometry at 450 nm. A melanin calibration range is prepared in parallel. The results are expressed as µg/ml of extracellular melanin and as a percentage of inhibition relative to the control group in Table 1 below.

Results:

TABLE 1 evaluation of the inhibition of extracellular melanin production for the compounds according to the invention and the compounds of the prior art.

| Test products | Extracellular melanin (control: 98 µg ± 4 µg/ml) | % Inhibition of extracellular melanin production relative to the control |
|---|---|---|
| Arbutin (40 µg/ml) (prior art) | 39 ± 3 | 61 |
| N-Undecylenoyl phenylalanine (MW = 331) (40 µg/ml) (prior art) | 59 ± 3 | 40 |
| N-Undecylenoyl phenylalanine (80 µg/ml) (prior art) | Cytotoxicity | Cytotoxicity |
| Compound (A) (40 µg/ml) | 84 ± 8 | 15 |
| Compound (A) (80 µg/ml) | 42 ± 1 | 58 |
| Compound (B) (80 µg/ml) | 54 ± 3 | 34 |

The results indicated in Table 1 demonstrate the depigmenting effect induced by compound A of example 1 and by compound B of example 2. They also demonstrate that at an equivalent molar concentration of N-undecylenoyl phenylalanine radical, the esterification of N-undecylenoyl alanine with glycerol or with diglycerol makes it possible to control the intensity of lightening of the skin, in contrast with the non-esterified product.

Study of the Cytotoxic Effect of the Compound of Formula (I) in B16/F1 melanocyte Cultures Evaluation of the presence of cytotoxic effects is performed using the Bradford technique by staining with Coomassie blue (Bradford M., "A rapid and sensitive method for the quantification of microgram quantities of protein utilizing the principle of protein-dye binding", Anal. Biochem., 1976, 72, 248-254). The B16/F1 melanocytes are incubated after seeding with the dilutions of the test products. After 72 hours of incubation, the B16/F1 melanocytes are washed and then lyzed, and Bradford's reagent is then added. After incubation for 5 minutes at room temperature, a spectrophotometric reading is taken at 640 nm in parallel with an albumin calibration range. The cytotoxicity is proven for a decrease greater than or equal to 20% of the total amount of protein. The results are expressed as a percentage decrease of the total amount of protein, in Table 2 below.

Results:

TABLE 2 evaluation of the total amount of protein relative to the control (albumin) for the compounds according to the invention and the compounds of the prior art.

| Test products | % Decrease of the total amount of protein relative to the control | Evaluation |
|---|---|---|
| N-Undecylenoyl phenylalanine (50 µg/ml) (prior art) | 32% | Cytotoxic |
| N-Undecylenoyl phenylalanine (80 µg/ml) (prior art) | 80% | Cytotoxic |
| Compound (A) (40 µg/ml) | No observed decrease | Not cytotoxic |
| Compound (A) (80 µg/ml) | No observed decrease | Not cytotoxic |
| Compound (B) (60 µg/ml) | No observed decrease | Not cytotoxic |
| Compound (B) (80 µg/ml) | No observed decrease | Not cytotoxic |

The results of Table 2 demonstrate the absence of cytotoxic effects for compound A of example 1 and for compound B of example 2, whereas, for a lower dose, N-undecylenoyl phenylalanine of the prior art proves to be cytotoxic.

Compound A of example 1 and compound B of example 2 are thus non-cytotoxic depigmenting compounds.

EXAMPLES OF COSMETIC FORMULATIONS

In the examples that follow, the proportions are expressed as weight percentages.

Example 6

Lightening Care Emulsion for Mature Skin

| | |
|---|---|
| Montanov ™ 202 | 02.00% |
| Montanov ™ 68 | 02.00% |
| Caprylic capric triglycerides | 10.00% |
| Squalane | 10.00% |
| Water | qs 100% |
| Compound of formula (Ia) | 01.00% |
| Sepigel ™ 305 | 00.70% |
| Magnesium ascorbyl phosphate | 02.00% |
| Sepicide ™ HB | 00.30% |
| Sepicide ™ CI | 00.20% |
| Fragrance | 00.50% |

Example 7

Lightening Firming care Emulsion

| | |
|---|---|
| Montanov ™ 202 | 03.00% |
| 24% sodium hydroxide | qs pH |
| Ethylhexyl methoxycinnamate | 06.00% |
| Lanol ™ 1688 | 08.00% |
| Benzophenone-3 | 04.00% |
| Water | qs 100% |
| Compound of formula (Ia) | 02.00% |
| Simulgel ™ NS | 00.50% |
| Sepilift ™ DPHP | 00.50% |
| Dimethicone | 02.00% |
| Cyclomethicone | 02.00% |
| Arbutin | 0.3% |
| Sepicide ™ HB | 00.30% |
| Sepicide ™ CI | 00.20% |
| Fragrance | 00.10% |

Example 8

Lightening Cream-gel Containing α-hydroxy Acids

| | |
|---|---|
| Hydroxyethylcellulose | 0.80% |
| Ethylhexyl octanoate | 05.00% |
| 60% sodium lactate | 14.00% |
| Water | qs 100% |
| Compound of formula (Ia) | 03.00% |
| Sepigel ™ 305 | 04.20% |
| Sepicide ™ HB | 02.00% |
| Sepicide ™ CI | 03.00% |
| Fragrance | 00.10% |

Example 9

Lightening Care Emulsion

| | |
|---|---|
| Montanov ™ L | 01.00% |
| Cetyl alcohol | 02.00% |
| Isodecyl neopentanoate | 12.00% |
| Cetaryl octanoate | 10.00% |
| Glycerol | 03.00% |
| Water | qs 100% |
| Compound of formula (Ia) | 01.00% |
| Simugel ™ EG | 02.00% |
| Kojic acid | 01.00% |
| Sepicide ™ HB | 00.30% |
| Sepicide ™ CI | 00.20% |
| Fragrance | 00.10% |

Example 10

Lightening Lotion

| | |
|---|---|
| Oramix ™ CG110 | 05.00% |
| Kathon ™ CG | 00.08% |
| Water | qs 100% |
| Compound of formula (Ia) | 01.00% |
| Fragrance | 00.10% |

This lotion may be sold in bottles or impregnated into wipes.

The definitions of the commercial products used in the examples are as follows:

Sepilift™ DPHP (INCI name: dipalmitoyl hydroxyproline), sold by the company SEPPIC.

Sepicide™ CI: imidazolidinylurea (preserving agent), sold by the company SEPPIC.

Sepicide™ HB: mixture of phenoxyethanol, methyl paraben, ethyl paraben, propyl paraben and butyl paraben (preserving agent) sold by the company SEPPIC.

Kathon™ CG (INCI name: methylisothiazolinone/methylchloroisothiazolinone).

Simulgel™ EG: self-invertible copolymer inverse latex such as those described in international publication WO 99/36445 (INCI name: sodium acrylate/sodium acryloyldimethyltaurate copolymer and isohexadecane and Polysorbate 80) sold by the company SEPPIC.

Simulgel™ NS: self-invertible copolymer inverse latex such as those described in international publication WO 99/36445 (INCI name: hydroxyethyl acrylate/sodium acryloyldimethyltaurate copolymer and squalane and Polysorbate 60) sold by the company SEPPIC.

Sepigel™ 305: self-invertible inverse latex (INCI name: polyacrylamide/C13-C14 isoparaffin/Laureth-7).

Lanol™ 1688: cetearyl ethylhexanoate, sold by the company SEPPIC.

Montanov™ L: emulsifier based on C14-C22 alcohol and on C12-C20 alkyl polyglucoside such as those described in European patent application EP 0 995 487.

Montanov™ 202 is an emulsifier based on arachidyl alcohol, behenyl alcohol and arachidyl polyglucoside.

Lanol™ 1688 is cetearyl ethylhexanoate, sold by the company SEPPIC.

Montanov™ 68 is an emulsifier based on cetearyl alcohol and cetearyl polyglucoside.

Oramix™ CG110 is a foaming agent based on octyl polyglucosides and decyl polyglucosides.

The invention claimed is:

1. A compound of formula (I):

in which m is an integer equal to 0 or 1 and p is an integer equal to 0, 1, 2 or 3.

2. A compound of formula ($I_a$):

corresponding to formula (I) as defined in claim 1, in which m is equal to 1.

3. A compound of formula ($I_{a1}$):

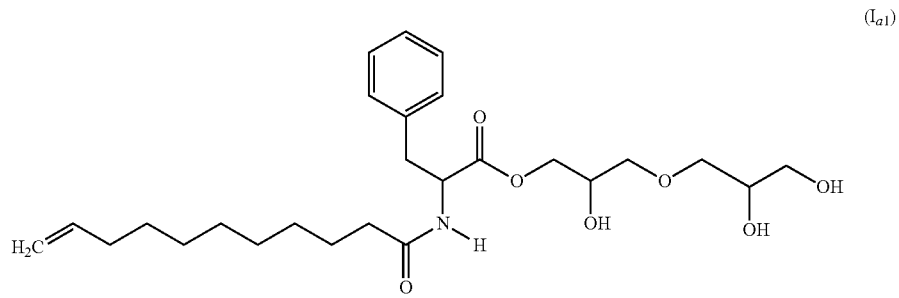

corresponding to formula ($I_a$) as defined in claim 2, in which p is equal to 1.

4. A compound of formula ($I_b$):

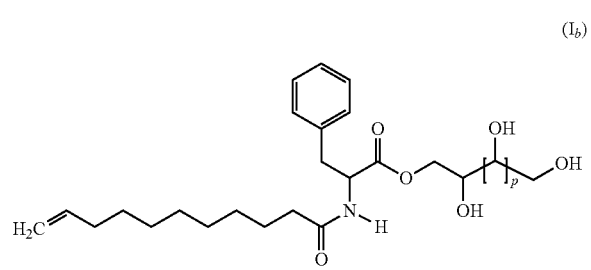

corresponding to formula (I) as defined in claim 1, in which m is equal to 0.

5. A compound of formula ($I_{b1}$):

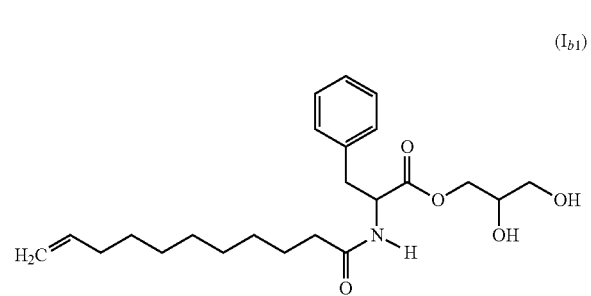

corresponding to formula ($I_b$) as defined in claim 4, in which p is equal to 0.

6. A compound of formula ($I_{b2}$):

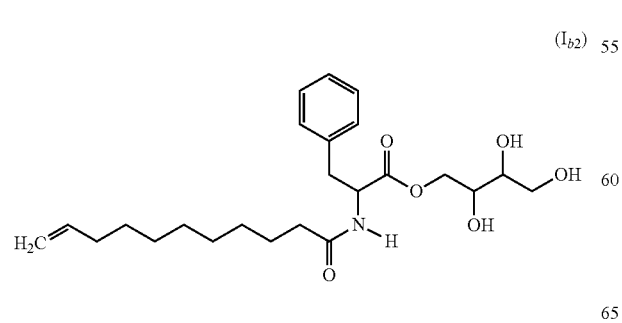

corresponding to formula ($I_b$) as defined in claim 4, in which p is equal to 1.

7. A compound of formula ($I_{b3}$):

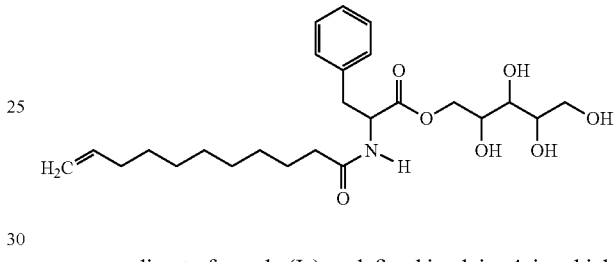

corresponding to formula ($I_b$) as defined in claim 4, in which p is equal to 2.

8. A compound of formula ($I_{b4}$)

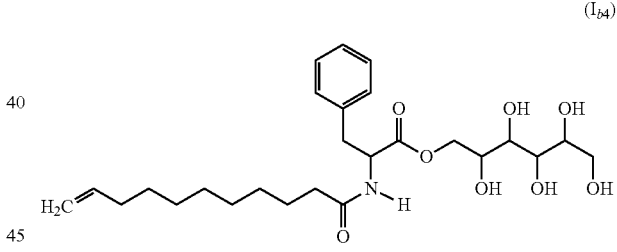

corresponding to formula ($I_b$) as defined in claim 4, in which p is equal to 3.

9. A process for preparing the compound of formula (I) as defined in claim 1, comprising: a step a) of esterification of the compound of formula (II):

with the polyol of formula (III):

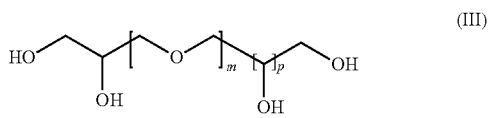

to form the compound of formula (I).

10. The process of claim 9, wherein the esterification of the compound of formula (II):

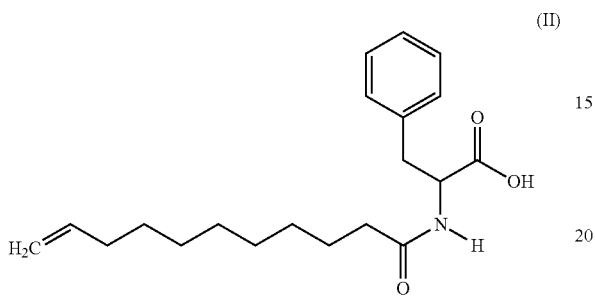

with the polyol of formula(III):

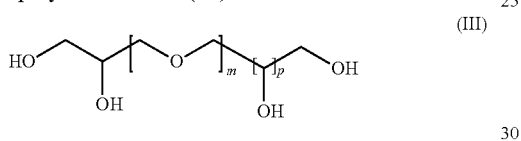

forms, in addition to the compound of formula(I), a compound of formula (IV):

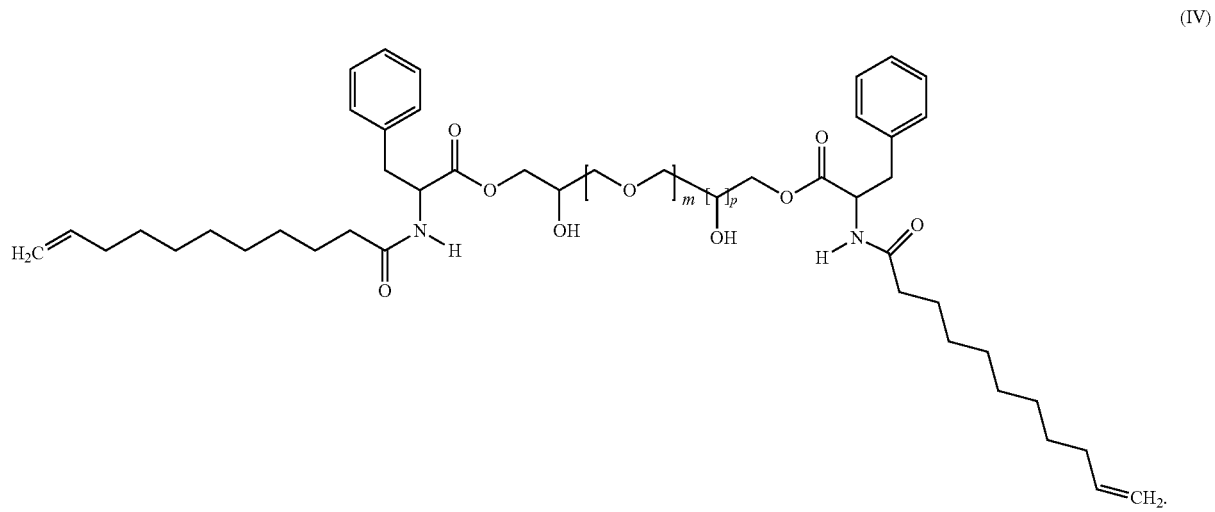

11. The process of claim 10, further comprising: a step b) of separation of said compound of formula (IV) and of said compound of formula (I).

12. A cosmetic composition comprising as lightening agent for human bodily skin an effective amount of a compound of formula (I) as defined in claim 1.

13. A non-therapeutic process for lightening human skin, comprising at least one step of applying to said human skin a cosmetic composition according to claim 12, wherein the composition is formulated for topical use.

14. A medicament with lightening activity on human bodily skin, comprising as active principle an effective amount of a compound of formula (I) as defined in claim 1.

15. A method of lightening human bodily skin comprising applying to said skin an effective amount of the compound of formula (I) as defined in claim 1.

16. A non-therapeutic process for lightening human skin, comprising at least one step of applying to said human skin a cosmetic composition for topical use comprising an effective amount of a compound of formula (I) as defined claim 1.

* * * * *